United States Patent [19]

Kane

[11] Patent Number: 5,654,187
[45] Date of Patent: Aug. 5, 1997

[54] MDR1 RETROVIRAL PLASMID

[75] Inventor: Susan E. Kane, Duarte, Calif.

[73] Assignee: The United States of America as represented by the Department of Health and Human Services, Washington, D.C.

[21] Appl. No.: 25,326

[22] Filed: Feb. 25, 1993

[51] Int. Cl.[6] ............................. C12N 5/10; C12N 15/86
[52] U.S. Cl. .................... 435/325; 435/320.1; 435/357
[58] Field of Search .................... 435/320.1, 69.1, 435/240.2; 935/22, 23, 32, 55, 66, 70

[56] References Cited

PUBLICATIONS

Miller et al., "Improved Retroviral Vectors for Gene Transfer and Expression", BioTechniques, vol. 7, No. 9 (1989) pp. 980–990.

Germann et al. "Retroviral Transfer of a Chimeric Multidrug Resistance–Adenosine Deaminase Gene", FASEB Journal, vol. 4, Mar. 1990, pp. 1501–1507.

Kane et al., "A New Vector Using the Human Multidrug Resistance Gene as a Selectable Marker Enables Overexpression of Foreign Genes in Eukaryotic Cells" Gene, vol. 84, 1989, pp. 439–446.

*Primary Examiner*—David Guzo
*Attorney, Agent, or Firm*—Needle & Rosenberg, P.C.

[57] ABSTRACT

Existing plasmids, such as pHaMDR/A (available from NIH) are large and cumbersome. The size may limit the known utility of MDR1 as an effective selectable marker in gene transfer experiments. The invention provides novel plasmids including heterologous promoters and cDNA sequences positioned between the retroviral LTRs.

8 Claims, 4 Drawing Sheets

MDR1 RETROVIRAL PLASMID

FIELD OF INVENTION

This invention relates to an improved retroviral plasmid which uses the human multidrug resistance gene (MDR1) as a selectable marker in gene transfer experiments.

BACKGROUND OF THE INVENTION

MDR1 has been described as an efficient, amplifiable, selectable marker in mammalian gene transfer experiments. Kane, S. E., et al., *Gene* 84:439–446 (1989). MDR1 based retroviruses have been used in mouse bone marrow transduction and reconstitution experiments to demonstrate long-term survival and in vivo selection of MDR1-marked hematopoietic cells. Sorrentino, B. P., et al., *Science* 257:99–103 (1992).

Existing MDR1 based plasmids, such as the plasmid HaMDR/A (available from NIH) are large and cumbersome. Pastan, I., et al., *Proc. Natl.Acad. Sci.USA* 85:4486–4490 (1988). The size of existing MDR1 plasmids may limit the known utility of MDR1 as an effective selectable marker in both in vitro and in vivo gene transfer experiments. Cloning manipulations involving such plasmids are difficult.

Current methods for using MDR1 to coexpress heterologous cDNAs in retroviral constructs require placing the heterologous cDNAs directly downstream of the MDR1 cDNA, for coexpression with MDR1 as a fusion gene and fusion protein. Germann, U. A., et al., *FASEB J.* 4:1501–1507 (1990). This construct may place severe limitations on the size of the fusion gene to be expressed. In addition, the eventual localization of the fusion gene product is limited, and independent regulation of expression of MDR1 and the heterologous gene of interest is not possible.

The amount of viral genetic information in known MDR1 based plasmids precludes insertion of a separate heterologous promoter and cDNA sequence between the retroviral long terminal repeats (LTRs) of the plasmid. However, placement of such sequences between the LTRs is a prerequisite to packaging into infectious retroviral particles for gene transfer to mammalian cells.

This invention reduces the overall size of the MDR1 plasmid and permits the insertion of a separate promoter to control expression of the heterologous cDNA.

The plasmids of the invention allow simultaneous expression and transfer of MDR1 (a selectable marker) plus other genes via retrovirus.

SUMMARY OF THE INVENTION

Novel plasmids of the invention include heterologous promoters and cDNA sequences between the retroviral LTRs. These plasmids permit the production and expression of retroviruses which include MDR1 as a selectable marker plus at least one other heterologous gene by cells cultured in vitro. The invention facilitates the use of MDR1 as a selectable marker in retrovirus-mediated gene transfer and gene therapy procedures.

In preferred embodiments of the invention, the novel plasmids include a number of unique restriction sites to facilitate modification.

One important aspect of the invention includes plasmids in which the cDNA sequence heterologous to MDR1 is a mammalian therapeutic sequence such as a sequence which expresses human glutathione-S-transferase (GST-π) or human glutathione peroxidase (CPX-1) for the production of engineered bone marrow cells and other cell types resistant to a broad range of drugs, genes which express human glucocerebrosidase or β-glucuronidase for the correction of metabolic defects, cDNA sequences which express human globins for correcting single gene defects as in sickle cell anemia or thalassemia and cDNA sequences which express ribozymes targeted against deliterious retroviral or oncogene RNA.

DETAILED DESCRIPTION OF THE INVENTION

The plasmids of this invention may be produced by known techniques. Retroviral sequences positioned between the LTRs of known MDR1 plasmids and which are non-functional may be deleted and replaced by genetic information, including a cDNA sequence heterologous to MDR1 and, if desired, unique restriction sites.

EXAMPLE I

Assembly of Plasmid HaMDR/A.MSHa Assembly of Upstream and Downstream LTRs

Figure 1:
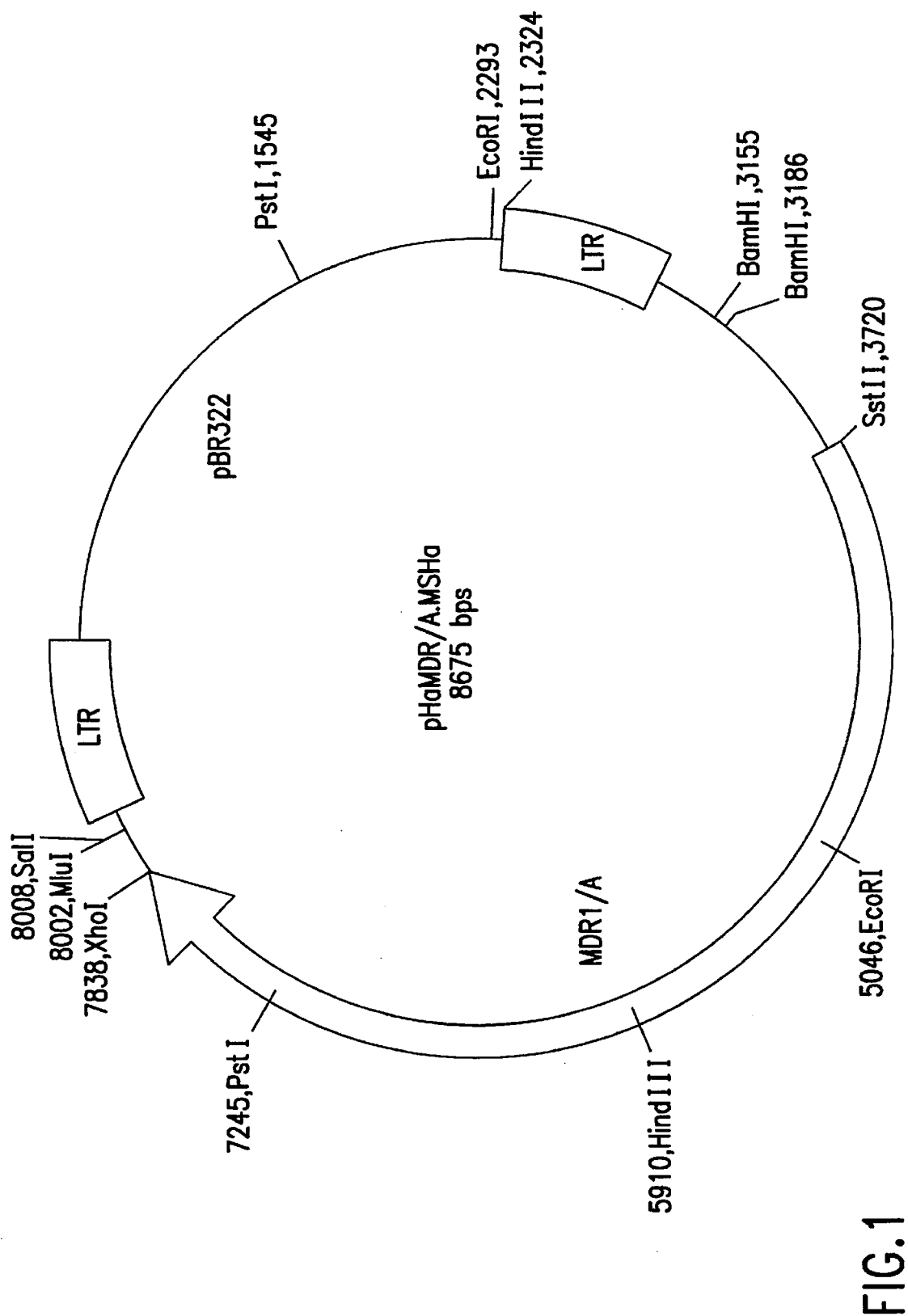
FIG. 1 depicts the plasmid HaMDR/A.MSHa with an indicated site for the insertion of heterologous cDNA sequences.
Figure 2:
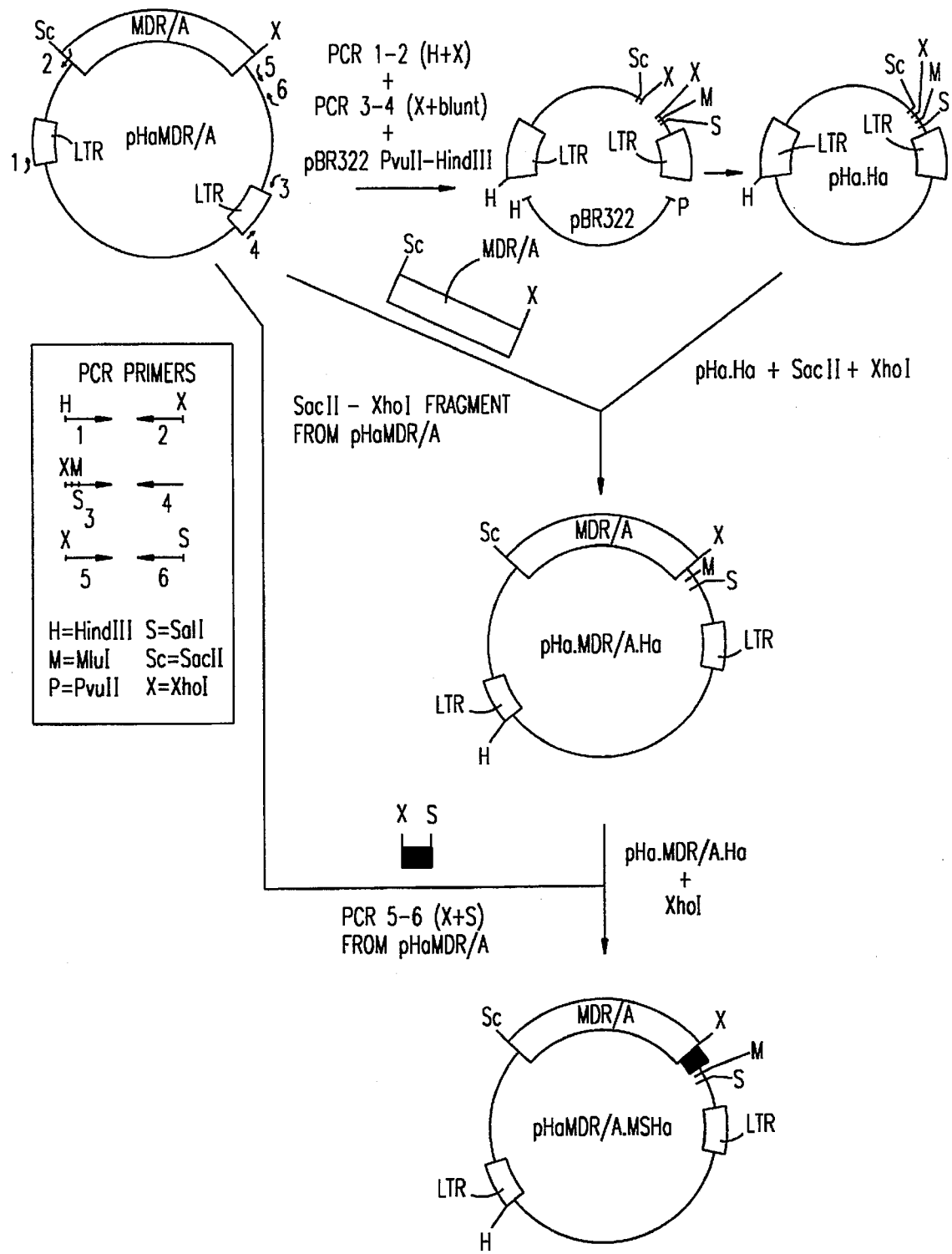
FIG. 2 depicts one series of steps useful to produce the new plasmid of FIG. 1 from the known plasmid HaMDR/A.

1. As FIG. 2 illustrates, PCR reactions were performed to amplify identified fragments of pHaMDR/A. Referring to the illustration of the plasmid HaMDR/A which appears in FIG. 1, the fragments to be amplified appear between the numbers 1–2, 3–4 and 5–6. The primer sequences for these fragments are set forth below:

| | |
|---|---|
| Primer 1 | 5'-ACGTGGAAGCTTAATGAAAGACCCCACC-3' (SEQ ID 1) |
| Primer 2 | 5'-ACGTGGCTCGAGCCGCGGCGGGTGC-3' (SEQ ID 2) |
| Primer 3 | 5'-ACGTGGCTCGAGACGCGTGTCGACAAGCCTATAGAG-3' (SEQ ID 3) |
| Primer 4 | 5'-CCAAATGAAAGACCCCC-3' (SEQ ID 4) |
| Primer 5 | 5'-CGTGGCTCGAGCCTCTAGATTCC-3' (SEQ ID 5) |
| Primer 6 | 5'-TGGGTCGACGTCAACAGTC-3' (SEQ ID 6) |

(a) For fragment 1–2, a HindIII site was included at the 5' end of the upstream PCR primer. A XhoI site was included at the 5' end of the downstream PCR primer. This fragment corresponds to the upstream LTR and retroviral packaging sequences. Fragment was digested at the 5' end with HindIII and at the 3' end with XhoI.

(b) Fragment 3–4 corresponds to the downstream LTR plus 60 bp on the upstream side of this LTR. XhoI, MluI and SalI sites were included at the 5' end of the upstream PCR primer, as indicated. Fragment was blunt-ended with T4 DNA polymerase and then digested at the 5' end with XhoI.

2. A PvuII-HindIII fragment was derived from pBR322. This fragment contains a bacterial origin of replication and ampicillin resistance gene. PvuII is a blunt-cutting enzyme.

3. These three fragments were ligated to give plasmid pHa. Ha shown in FIG. 2.

Insertion of MDR/A cDNA

The MDR1 cDNA lacking its own polyadenylation signal (MDR/A) was isolated from pHaMDR/A as a SacII-XhoI fragment, and inserted into the SacII-XhoI site of pHa. Ha resulting in plasmid pHa.MDR/A.Ha.

Insertion of Downstream Transcription Enhancer Element

It has previously been reported that plasmid sequences in pHaMDR/A, downstream from MDR1, are essential for expression of that gene. These sequences were isolated on a PCR fragment, using pHaMDR/A as a template and the oligos indicated for PCR 5–6 in FIG. 2. The viral enhancer element so isolated corresponds to nucleotides 2022–2173 on the Ha-MSV genomic sequence. *RNA Tumor Viruses,* Second Edition, Supplements and Appendices. Weiss et al. (eds.). Cold Spring Harbor Laboratory, Cold Spring Harbor, N.Y., pp. 928–939 (1985). The indicated XhoI site was included in the upstream PCR oligo while a SalI site was included at the 5' end of the downstream PCR oligo. The PCR fragment was digested with SalI plus XhoI and inserted into the XhoI site of pHa.MDR/A.Ha in the figure creating the final plasmid, pHaMDR/A.MSHa. The SalI cohesive end is compatible with that of XhoI, but no functional restriction site is reconstituted by this ligation, so the XhoI site at the 5' end of the transcription enhancer element and the 3' end of the MDR/A cDNA remains a unique site in pHaMDR/A.MSHa. SacII, MluI and SalI are also unique sites.

EXAMPLE II

Production of Retrovirus With Plasmid HaMDR/A.MSHa

The plasmid HaMDR/A.MSHa or the known plasmid, HaMDR/A, was transfected using the calcium phosphate-DNA co-precipitation method (Graham, F., et al., *Virology* 52:456–457 (1973)) into packaging cell lines which expressed retrovirus particles in the cell culture medium. Packaging cell lines used were either PA317 (Miller, A. D., et al., *Mol. Cell. Biol.* 6:2895–2902 (1986)) or GP+E86 (Markowitz, D., et al., *J.Virol.* 62:1120–1124 (1988)) cells, grown in DMEM+10% fetal bovine serum. Two days following transfection, cells were trypsinized and plated in either 20 ng/ml (GP+E86) or 30 ng/ml (PA317) colchicine to select for cells which had taken up and expressed MDR1. After 10–14 days of selection, colchicine-resistant colonies were pooled and growth in colchicine was continued for 2–3 passages. To collect MDR1 retrovirus, cells were grown to 80% confluence, fresh culture medium lacking colchicine was added, and then collected after 18–22 hrs. Collections were spun for 5 min. at 5000×g to remove cells, and viral supernatants were stored frozen at −80° C.

Retrovirus titers were determined for pHaMDR/A and pHaMDR/A.MSHa virus, obtained from either PA317 or GP+E86 cells, as follows:

1. On day 0, NIH 3T3 cells were plated at $5\times10^4$ cells per 60 mm dish.

2. On day 1, 100 µaliquots of 10-fold serials dilutions of virus were added to cells, in the presence of 8 µg/ml polybrene.

3. On day 3, virus was removed and medium containing 60 ng/ml colchicine was added, to select for cells transduced with MDR1 retrovirus.

4. After 8–10 days, drug resistant colonies were stained with methylene blue and counted.

The following retroviral titers (colony forming units per ml) were obtained. Values are averages of the number of experiments indicated in parentheses after each titer.

|  | PA317 | GP + E86 |
| --- | --- | --- |
| pHaMDR/A.MSHa | $3.0 \times 10^2$ (1) | $5.4 \times 10^4$ (2) |
| pHaMDR/A (known plasmid) | $1.8 \times 10^4$ (4) | $1.4 \times 10^6$ (3) |

Described below is a qualitative demonstration that the pHaMDR/A.MSHa plasmid is capable of supporting MDR1 retrovirus production:

1. On day 0, NIH 3T3 cells were plated at $2\times10^4$ cells per 35 mm dish.

2. On day 1, 500 µof appropriate retroviral collections were added to cells in the presence of 8 µg/ml polybrene.

3. On day 3, virus was removed, and cells were processed to detect cell surface expression of the MDR1 gene product (P-glycoprotein). Cell surface detection was performed by indirect immunofluoroesence (Kane, S. E., et al., *Gene* 84:439–446 (1989)) using an antibody specific for an external epitope of P-glycoprotein.

Selected results of this analysis are shown in FIGS. 4A, 4B, 4C and 4D. Cells in FIGS. 4A and 4B were transduced with retrovirus derived from pHaMDR/A.MSHa plasmid (viral titers of $2.8\times10^4$ and $8.1\times10^4$, respectively) while cells in FIGS. 4C and 4D were transduced with retrovirus derived from the known pHaMDR/A plasmid (viral titers of $6.7\times10^5$ and $2.8\times10^6$, respectively). Results demonstrate that comparable levels of expression of P-glycoprotein were obtained with virus derived from either MDR1 plasmid.

EXAMPLE III

Assembly of Plasmid HaMDR/A.SVHa

Plasmid HaMDR/A.SVHa was derived directly from plasmid HaMDR/A.MSHa as follows:

1. A restriction fragment containing the SV40 viral early promoter was isolated by digesting plasmid pSK1.MDR (Kane, S. E., et al., *Gene* 84:439–446 (1989)) with MluI and SalI and purifying a 340 bp fragment with MluI cohesive 5' end and SalI cohesive 3' end.

2. Plasmid HaMDR/A.MSHa was digested with MluI and SalI, unique restriction sites located as shown in FIG. 2. Plasmid was treated with calf intestinal phosphatase to remove phosphates.

Figure 3:
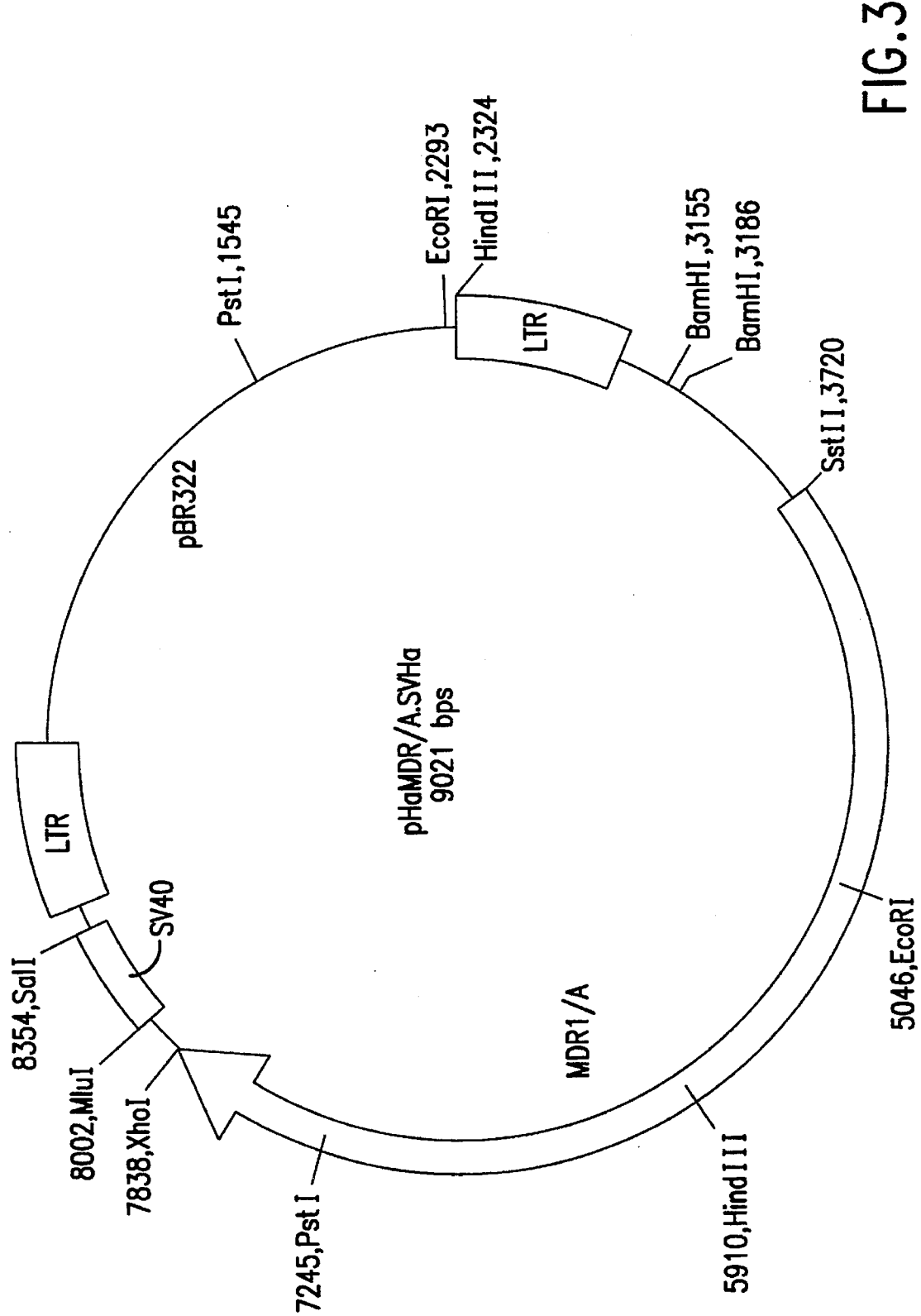
FIG. 3 depicts the plasmid HaMDR/A.SVHa.
Figure 4A:
FIGS. 4A, 4B, 4C and 4D are reproductions of photographs which demonstrate that the plasmid depicted by FIG. 1 supports MDR1 retrovirus production at a level comparable to that produced by the known plasmid HaMDR/A.
Figure 4B:
Figure 4C:
Figure 4D:
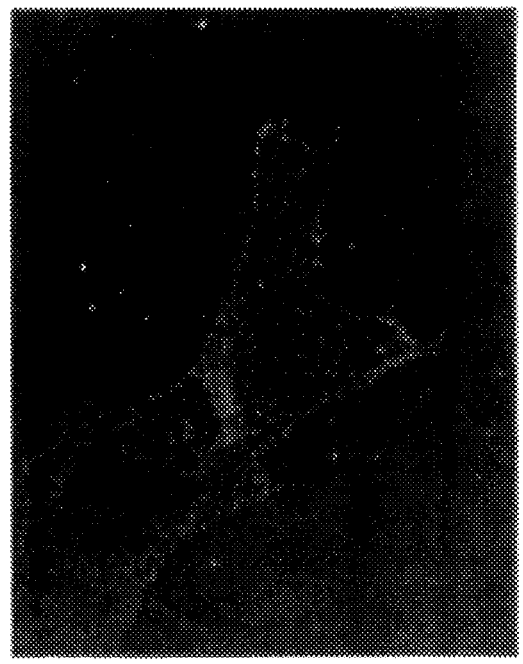

3. Plasmid and purified SV40 promoter fragment were ligated and HB101 bacteria were transformed. Resulting colonies were screened for the appropriate construction, which is illustrated in FIG. 3.

Insertion of Heterologous cDNA Sequences

Heterologous cDNA sequences are inserted into pHaMDR/A.SVHa using standard cloning techniques. The unique SalI restriction site serves as the position for inserting cDNAs. SalI sites are added to the end of heterologous cDNA fragments either by ligation with SalI linkers or by PCR with SalI sites in the oligonucleotide primers. After ligation and bacterial transformation with pHaMDR/A.SVHa and cDNA, the orientation of cDNA in the plasmid is determined by restriction digestion, using convenient restriction sites within the heterologous cDNA and those shown on FIG. 3 for this analysis.

I claim:

1. A Harvey murine sarcoma virus MDR1 retroviral plasmid having first and second long terminal repeats and at least one heterologous promoter and a cDNA sequence heterologous to MDR1 positioned between said long terminal repeats, wherein the promoter and the cDNA sequence are each positioned in the direction of transcription from only the first long terminal repeat.

2. The MDR1 retroviral plasmid of claim 1 in which the cDNA sequence heterologous to MDR1 is a mammalian therapeutic sequence.

3. A cell transduced with virus derived from the plasmid of claim 1.

4. The plasmid HaMDR/A.MSHa.

5. The plasmid HaMDR/A.SVHa.

6. A cell transduced with virus derived from the plasmid of claim 4.

7. A cell transduced with virus derived from the plasmid of claim 5.

8. Packaging cell line PA317 or packaging cell line GP+E86 transfected with a plasmid as defined by claim 1, claim 4 or claim 5.

* * * * *

SEQUENCE LISTING ( 1 ) GENERAL INFORMATION:

( i i i ) NUMBER OF SEQUENCES: 6

( 2 ) INFORMATION FOR SEQ ID NO: 1:

( i ) SEQUENCE CHARACTERISTICS:
        ( A ) LENGTH: 28
        ( B ) TYPE: Nucleic Acid
        ( C ) STRANDEDNESS: Single
        ( D ) TOPOLOGY: Unknown ( i i ) MOLECULE TYPE: DNA ( i i i ) HYPOTHETICAL: No ( i v ) ANTI-SENSE: No ( v ) FRAGMENT TYPE: Not Applicable ( v i ) ORIGINAL SOURCE: Synthetically Prepared ( v i i ) IMMEDIATE SOURCE: Synthetically Prepared ( v i i i ) POSITION IN GENOME: None ( i x ) FEATURE: None ( x ) PUBLICATION INFORMATION: None ( x i ) SEQUENCE DESCRIPTION: SEQ ID NO: 1:

ACGTGGAAGC TTAATGAAAG ACCCCACC        28

( 2 ) INFORMATION FOR SEQ ID NO: 2:

( i ) SEQUENCE CHARACTERISTICS:
        ( A ) LENGTH: 25
        ( B ) TYPE: Nucleic Acid
        ( C ) STRANDEDNESS: Single
        ( D ) TOPOLOGY: Unknown ( i i ) MOLECULE TYPE: DNA ( i i i ) HYPOTHETICAL: No ( i v ) ANTI-SENSE: No ( v ) FRAGMENT TYPE: Not Applicable ( v i ) ORIGINAL SOURCE: Synthetically Prepared ( v i i ) IMMEDIATE SOURCE: Synthetically Prepared ( v i i i ) POSITION IN GENOME: None ( i x ) FEATURE: None ( x ) PUBLICATION INFORMATION: None ( x i ) SEQUENCE DESCRIPTION: SEQ ID NO: 2:

ACGTGGCTCG AGCCGCGGCG GGTGC        25

( 2 ) INFORMATION FOR SEQ ID NO: 3:

(i) SEQUENCE CHARACTERISTICS:
            (A) LENGTH: 36
            (B) TYPE: Nucleic Acid
            (C) STRANDEDNESS: Single
            (D) TOPOLOGY: Unknown (ii) MOLECULE TYPE: DNA (iii) HYPOTHETICAL: No (iv) ANTI-SENSE: No (v) FRAGMENT TYPE: Not Applicable (vi) ORIGINAL SOURCE: Synthetically Prepared (vii) IMMEDIATE SOURCE: Synthetically Prepared (viii) POSITION IN GENOME: None (ix) FEATURE: None (x) PUBLICATION INFORMATION: None (xi) SEQUENCE DESCRIPTION: SEQ ID NO: 3:

ACGTGGCTCG AGACGCGTGT CGACAAGCCT ATAGAG                            36

(2) INFORMATION FOR SEQ ID NO: 4:

(i) SEQUENCE CHARACTERISTICS:
            (A) LENGTH: 17
            (B) TYPE: Nucleic Acid
            (C) STRANDEDNESS: Single
            (D) TOPOLOGY: Unknown (ii) MOLECULE TYPE: DNA (iii) HYPOTHETICAL: No (iv) ANTI-SENSE: No (v) FRAGMENT TYPE: Not Applicable (vi) ORIGINAL SOURCE: Synthetically Prepared (vii) IMMEDIATE SOURCE: Synthetically Prepared (viii) POSITION IN GENOME: None (ix) FEATURE: None (x) PUBLICATION INFORMATION: None (xi) SEQUENCE DESCRIPTION: SEQ ID NO: 4:

CCAAATGAAA GACCCCC                                                 17

(2) INFORMATION FOR SEQ ID NO: 5:

(i) SEQUENCE CHARACTERISTICS:
            (A) LENGTH: 23
            (B) TYPE: Nucleic Acid
            (C) STRANDEDNESS: Single
            (D) TOPOLOGY: Unknown (ii) MOLECULE TYPE: DNA (iii) HYPOTHETICAL: No (iv) ANTI-SENSE: No (v) FRAGMENT TYPE: Not Applicable (vi) ORIGINAL SOURCE: Synthetically Prepared (vii) IMMEDIATE SOURCE: Synthetically Prepared -continued (viii) POSITION IN GENOME: None (ix) FEATURE: None (x) PUBLICATION INFORMATION: None (xi) SEQUENCE DESCRIPTION: SEQ ID NO: 5:

CGTGGCTCGA GCCTCTAGAT TCC  23

(2) INFORMATION FOR SEQ ID NO: 6:

(i) SEQUENCE CHARACTERISTICS:
 (A) LENGTH: 19
 (B) TYPE: Nucleic Acid
 (C) STRANDEDNESS: Single
 (D) TOPOLOGY: Unknown (ii) MOLECULE TYPE: DNA (iii) HYPOTHETICAL: No (iv) ANTI-SENSE: No (v) FRAGMENT TYPE: Not Applicable (vi) ORIGINAL SOURCE: Synthetically Prepared (vii) IMMEDIATE SOURCE: Synthetically Prepared (viii) POSITION IN GENOME: None (ix) FEATURE: None (x) PUBLICATION INFORMATION: None (xi) SEQUENCE DESCRIPTION: SEQ ID NO: 6:

TGGGTCGACG TCAACAGTC  19